(12) United States Patent
Cerny et al.

(10) Patent No.: US 7,977,046 B2
(45) Date of Patent: Jul. 12, 2011

(54) METHOD OF SELECTING DNA CONSTRUCTS FOR HERBICIDE TOLERANCE IN PLANTS

(75) Inventors: R. Eric Cerny, Chesterfield, MO (US); Sophia Y. (Yun Chia) Chen, Chesterfield, MO (US); Jeanne G. Layton, Chesterfield, MO (US); Bernard Sammons, Ellisville, MO (US); R. Douglas Sammons, New Melle, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1370 days.

(21) Appl. No.: 10/332,494

(22) PCT Filed: May 10, 2002

(86) PCT No.: PCT/US02/14793
§ 371 (c)(1),
(2), (4) Date: Jan. 8, 2003

(87) PCT Pub. No.: WO02/092856
PCT Pub. Date: Nov. 21, 2002

(65) Prior Publication Data
US 2004/0060078 A1    Mar. 25, 2004

Related U.S. Application Data

(60) Provisional application No. 60/291,192, filed on May 15, 2001.

(51) Int. Cl.
*C12Q 1/68* (2006.01)
(52) U.S. Cl. ............................................... 435/6
(58) Field of Classification Search .................. None
See application file for complete search history.

(56) References Cited

U.S. PATENT DOCUMENTS

| | | | |
|---|---|---|---|
| 4,535,060 A | 8/1985 | Comai | |
| 4,810,648 A | 3/1989 | Stalker | |
| 5,094,945 A | 3/1992 | Comai | |
| 5,463,175 A | 10/1995 | Barry et al. | |
| 5,554,798 A | 9/1996 | Lundquist et al. | |
| 5,565,347 A | 10/1996 | Fillatti et al. | |
| 5,589,583 A * | 12/1996 | Klee et al. ............. | 800/298 |
| 5,627,061 A | 5/1997 | Barry et al. | |
| 5,633,435 A * | 5/1997 | Barry et al. ............. | 800/288 |
| 5,846,797 A | 12/1998 | Strickland | |
| 6,040,497 A | 3/2000 | Spencer et al. | |
| 6,762,344 B1 | 7/2004 | Spencer et al. | |
| 7,314,970 B2 | 1/2008 | Spencer et al. | |

FOREIGN PATENT DOCUMENTS

| | | |
|---|---|---|
| WO | WO 92/00377 A1 | 1/1992 |
| WO | WO 92/04449 A1 | 3/1992 |
| WO | WO 00/36911 A2 | 6/2000 |
| WO | WO 00/42207 A2 | 7/2000 |

OTHER PUBLICATIONS

Bechtold et al., "In planta agrobacterium mediated gene transfer by infiltration of adult arabidopsis thaliana plants," *Cr Acad. Sci. Paris. Life Sci.*, 316:1194-1199, 1993.
DeBlock et al., "Engineering herbicide resistance in plants by expression of a detoxifying enzyme," *EMBO J.*, 6:2513-2519, 1987.
Kahl, "Plant genetic engineering for crop improvement," *World J. of Microbiol. and Biotechnology*, 11:449-460, 1995.
Kishore et al., "Amino acid biosynthesis inhibitors as herbicides," *Ann. Rev. Biochem.*, 57:627-663, 1988.
Kishore et al., "5-enolpyruvylshikimate 3-phosphate synthase, from biochemistry to genetic engineering of glyphosate tolerance," In: Biotechnology for Crop Protection, ACS Symposium Series No. 379 Hedlin et al. (Eds.) pp. 37-48, 1988.
Misawa et al., "Functional expression of the erwinia uredovora carotenoid biosynthesis gene crtl in transgenic plants showing an increase of β-carotene biosynthesis activity and resistance to the bleaching herbicide norflurazon," *Plant J.*, 4:833-840, 1993.
Padgette et al., "New weed control opportunities: development of soybeans with a Roundup Ready™ Gene," In: Herbicide Resistant Crops, Lewis Publishers, pp. 53-88, 1996.
Penaloza-Vazquez et al., "Expression of the hygromycin B. phosphotransferase gene confers tolerance to the herbicide glyphosate," *Plant Cell Reports*, 14:482-487, 1995.
Potrykus, "Gene transfer to plants: assessment of published approaches and results," *Annu. Rev. Plant Physiol. Plant Mol. Biol.*, 42:205-225, 1991.
Sathasivan et al., "Nucleotide sequence of a mutant acetolactate synthase gene from an imidazolinone-resistant arabidopsis thaliana var. columbia," *Nucl. Acids Res.*, 18:2188, 1990.
Schulz et al., "Insensitivity of 5-enolpyruvylshikimic acid-3-phosphate synthase to glyphosate confers resistance to this herbicide in a strain of aerobacter aerogenes," *Arch. of Microbiol.*, 137:121-123, 1984.
Shah et al., "Engineering herbicide tolerance in transgenic plants," *Science*, 233:478-481, 1986.
Sost et al., "Characterization of a glyphosate-insensitive 5-enolpyruvylshikimic acid-3-phosphate synthase," *FEBS Letters*, 173:238-242, 1984.
Zhou et al., "Glyphosate-tolerant CP4 and GOX genes as a selectable marker in wheat transformation," *Plant Cell Rep.*, 15:159-163, 1995.

* cited by examiner

*Primary Examiner* — David H Kruse
(74) *Attorney, Agent, or Firm* — SNR Denton US LLP; Pamela J. Sisson, Esq.

(57) ABSTRACT

An improved method for selecting among DNA constructs conferring herbicide tolerance for those which confer superior vegetative and reproductive tolerance in crop plants. Additionally, an improved method for selecting among DNA constructs conferring herbicide tolerance for those which confer superior tolerance in vegetative tissues of crop plants but little or no tolerance in male reproductive tissues of crop plants for the purpose of producing male sterile plants useful in a hybrid crop production system.

4 Claims, 12 Drawing Sheets

METHOD OF SELECTING DNA CONSTRUCTS FOR HERBICIDE TOLERANCE IN PLANTS

This application claims the benefit of U.S. provisional application 60/291,192, filed May 15, 2001.

FIELD OF THE INVENTION

This invention relates in general to plant molecular biology and plant genetic engineering for herbicide tolerance and, more particularly, to a method for selecting DNA constructs with enhanced herbicide tolerance performance in transgenic crop plants from a plurality of DNA constructs. The invention more particularly is related to the use of transgenic model plants and the measurement of herbicide tolerance phenotypes to select DNA constructs that are useful in crop plants.

BACKGROUND OF THE INVENTION

One of the goals of plant genetic engineering is to produce plants with agronomically important characteristics or traits. Recent advances in genetic engineering have provided the requisite tools to produce transgenic plants that contain and express foreign genes (Kahl et al., World J. of Microbiol. Biotech. 11:449-4160, 1995). Particularly desirable traits or qualities of interest for plant genetic engineering would include but are not limited to resistance to insects, fungal diseases, and other pests and disease-causing agents, tolerances to herbicides, enhanced stability or shelf-life, yield, environmental tolerances, and nutritional enhancements. The technological advances in plant transformation and regeneration have enabled researchers to take exogenous DNA, such as a gene or genes from a heterologous or a native source, and incorporate the exogenous DNA into the plant's genome. In one approach, expression of a novel gene that is not normally expressed in a particular plant or plant tissue may confer a desired phenotypic effect. In another approach, transcription of a gene or part of a gene in an antisense orientation may produce a desirable effect by preventing or inhibiting expression of an endogenous gene.

In order to produce a transgenic crop plant, a DNA construct that includes a heterologous gene sequence is introduced into a crop plant cell. The plant cell is then regenerated to produce a transgenic crop plant. The DNA construct includes a plant promoter that is operably linked to the heterologous gene sequence, often a promoter not normally associated with the heterologous gene. The promoter controls expression of the introduced DNA sequence to which the promoter is operably linked and thus affects the desired characteristic conferred by the DNA sequence. However, the exact level of expression of the new phenotype and its subsequent commercial utility in the crop plant is generally not known until the DNA construct has been successfully introduced into the target crop. Transgenic crop plants are usually difficult, time consuming and expensive to transform, with cotton and soybeans being leading examples. When a large number of DNA constructs need to be tested for efficacy in a particular crop plant, it requires many resources to produce the large number of plants necessary to adequately screen the DNA constructs for the most effective one or two. Alternatively, one could produce only a few plants with each DNA construct to study their properties and then follow that step with another round of transformation to obtain the large number of transformation events usually required to obtain one line with the desirable characteristics necessary for commercial success. This choice requires a longer time to reach the desired result, having two rounds of transformation in a crop plant. It would be advantageous to have a rapid method of testing these many DNA constructs and selecting from these a small number that will perform in a crop plant at a useful level. A large number of transgenic crop plants can then be produced from the selected few DNA constructs, thus increasing the probability of identifying the most useful lines.

There are many varieties of promoters and other regulatory elements that affect the transgene expression such that a gene or genes is transcribed efficiently at the right time during plant growth and development, in the optimal location the plant, and in the amount necessary to produce the desired effect. The level and rate of transcription of the transgene of interest is controlled by the various genetic elements of the transgene expression cassette. Promoters, introns, and leaders affect the expression level of the gene of interest, as well as the tissue localization, which is especially important for herbicide tolerance genes. It has been particularly difficult to predict the performance of DNA constructs for herbicide tolerance at a whole crop plant level. Low levels of tolerance in the reproductive parts of the plant can result in a plant that apparently survives the herbicide treatment but does not produce economically sufficient quantities of the product of interest such as oilseeds or fiber. This has resulted in the need to provide multiple combinations of genetic elements operably linked in DNA constructs, then testing these in crop plants for their ability to confer the desired herbicide tolerance phenotype. Generally, large numbers of transgenic crop plants have to be produced in order to select the individual lines with commercially acceptable herbicide tolerance, it is impractical to incur the time and expense of testing many DNA constructs in crop plants that result in no usable lines. In addition, increasingly stringent government regulatory requirements on the contents of DNA constructs used for plant transformation and the insertion of expression cassettes into the plant genome makes it necessary to select plant lines from a large number of candidate lines and include backup lines to comply with the requirements. In this regulatory environment, resources cannot be wasted on DNA constructs that do not provide the requisite attributes. Therefore, an unmet need in genetic engineering of plants for herbicide tolerance is a rapid method to screen large numbers of DNA constructs in a transgenic model plant system, one that reflects the performance of the DNA constructs in various target crop plants.

Additionally, the commercial development of genetically improved germplasm has also advanced to the stage of introducing multiple traits into crop plants, often referred to as a gene stacking approach. In this approach, multiple genes conferring different characteristics of interest can be introduced into a plant. It is important when introducing multiple genes into a plant that each gene has been selected from the many possible combinations of elements so that the desired phenotype can be effectively expressed in the target crop plant. It is apparent that there is a need for a model transgenic plant system that is indicative of the performance of a DNA construct in a target crop plant for stacking gene traits.

*Arabidopsis thaliana* has a long history of use as a model plant to test the expression pattern of individual promoters, usually by placing them 5' to a reporter gene such as GUS, and the expression of transgenes. Also, many useful genes have been isolated from *Arabidopsis* and transferred to crop plant species. However, even though *Arabidopsis* genes have been isolated and transferred to other plants and DNA constructs having heterologous DNA sequences have been transformed into *Arabidopsis*, there has not been an effort to develop a system where *Arabidopsis* is used for the purpose of selecting from a number of possibly efficacious DNA constructs comprising a herbicide tolerance gene, a smaller number that would then be transformed into a crop plant of interest. The method of the present invention provides a process for selecting DNA constructs that have the greatest potential for producing herbicide tolerance in crop plants.

SUMMARY OF THE INVENTION

The present invention provides a method of selecting a DNA construct effective for conferring herbicide tolerance in crop plants from a plurality of DNA constructs by screening the constructs for efficacy in a transgenic model plant. The method includes the steps of: transforming a plant cell of a model plant with DNA constructs, each comprising a herbicide tolerance gene, regenerating the plant cell into a whole plant, treating the plant with an effective dose of the herbicide prior to flower formation, and scoring the plant for vegetative and reproductive fertility. If one or more of the DNA construct provides a high level of vegetative and reproductive herbicide tolerance in the model plant, then the construct or constructs are transformed into a crop plant cell, the crop plant cell is regenerated into a whole crop plant. The crop plant is treated with an effective dose of the herbicide and further propagated to provide seeds and plants to cross with crop plants of the same species. Thus, the transgenic model plant provides a high throughput testing system from which efficacious DNA constructs can be selected prior to transformation into crop plants.

One embodiment of the invention uses an *Arabidopsis* species as the model plant, preferably *A. thaliana*. Another embodiment of the invention uses micro-tomato as the model plant. Other easily transformable, non-crop plants may also be used.

According to one aspect of the invention, DNA constructs comprising a herbicide tolerance gene coding sequence can be any coding sequence that confers transgenic plant cell tolerance to herbicides. Examples of such herbicides are glyphosate, glufosinate, sulfonylureas, arylphenoxyproprionates, imidazolinones, bromozynil, delapon, cyclohezanedione, protoporphyrionogen oxidase inhibitors, or isoxaslutole herbicides. Preferably, the coding sequences would encode for herbicide resistant enzymes or enzymes that degrade or detoxify the herbicide when expressed in plant cells. These coding sequences include, but are not limited to, native and modified plant EPSP synthases, native and modified bacterial EPSP synthases, glyphosate oxidoreductase, glutamine synthetase, phosphinothricin acetyltransferase, modified plant acetolactate synthase, modified acetyl coenzyme A carboxylase. More preferably, the herbicide tolerance gene coding sequence encodes an EPSP synthase conferring high tolerance to glyphosate herbicide while maintaining good enzymatic characteristics such as the CP4 EPSP syntnase disclosed in U.S. Pat. No. 5,633,435, incorporated herein by reference.

According to one aspect of the invention, the DNA constructs selected by the method of the present invention provide complete vegetative and reproductive herbicide tolerance to the crop plant.

According to another aspect of the invention, the DNA constructs selected by the method of the present invention provide complete vegetative tolerance to the herbicide and incomplete reproductive tolerance to the crop plant, thereby providing a conditional sterility trait to the crop plant that is useful for hybrid seed production.

According to another aspect of the invention, the crop species is selected from the dicot crops that include, but are not limited to, cotton, soybean, canola, tomato, and alfalfa. Alternatively, the crop is selected from monocot crops that include, but are not limited to, corn, wheat, rice, barley, lettuce, and turf grasses.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
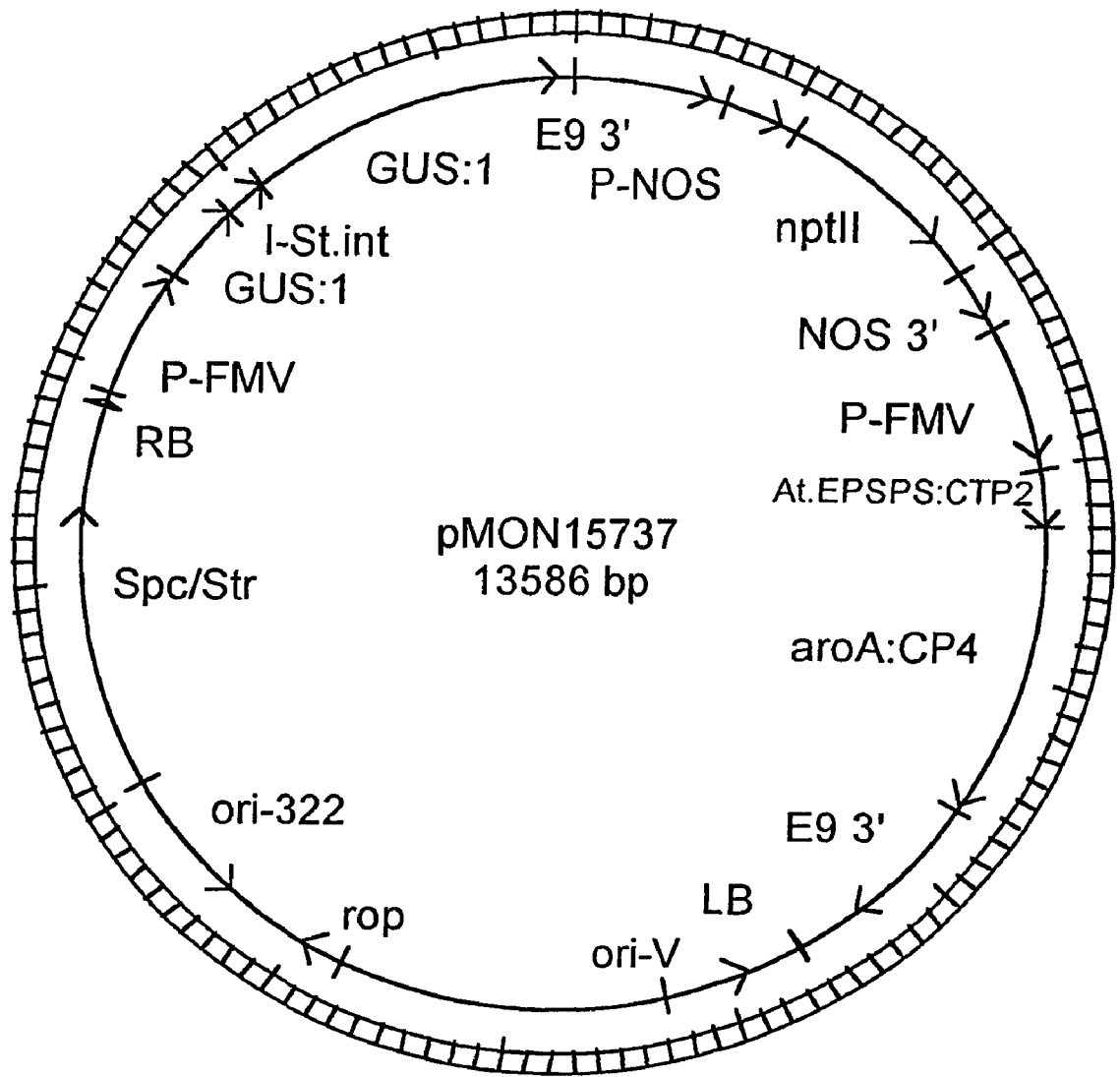
FIG. 1. Plasmid map of pMON15737
FIG. 2. Plasmid map of pMON26140
FIG. 3. Plasmid map of pMON40500
FIG. 4. Plasmid map of pMON40501
FIG. 5. Plasmid map of pMON51915
FIG. 6. Plasmid map of pMON52059
FIG. 7. Plasmid map of pMON52060
FIG. 8. Plasmid map of pMON52065
FIG. 9. Plasmid map of pMON54042
FIG. 10. Plasmid map of pMON54045
FIG. 11. Plasmid map of pMON54047
FIG. 12. Plasmid map of pMON54049

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., Glossary of Genetics: Classical and Molecular, 5th edition, Springer-Verlag: New York (1991); and Lewin. Genes V, Oxford University Press: New York (1994). The nomenclature for DNA bases as set forth at 37 CFR §1.822 is used. The standard one- and three-letter nomenclature for amino acid residues is used.

Abbreviations for nucleotide bases in nucleic acid codes as used herein are: A=adenosine; C=cytosine; G=guanosine; T=thymidine. Codes used for synthesis of oligonucleotides as used herein are: N=equimolar A, C, G, and T; I=deoxyinosine; K=equimolar G and T; R=equimolar A and G; S=equimolar C and G; W=equimolar A and T; Y=equimolar C and T.

"Nucleic acid (sequence)" or "polynucleotide (sequence)" refers to single- or double-stranded DNA or RNA of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "substantially purified", as used herein, refers to a molecule separated from other molecules normally associated with it in its native state. More preferably, a substantially purified molecule is the predominant species present in a preparation. A substantially purified molecule may be greater than 60% free, preferably 75% free, more preferably 90% free from the other molecules (exclusive of solvent) present in the natural mixture. The term "substantially purified" is not intended to encompass molecules present in their native state.

A first nucleic acid sequence displays "substantially identity" to a reference nucleic acid sequence if, when optimally aligned (with appropriate nucleotide insertions or deletions totaling less than 20 percent of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman, Adv. Appl. Math. 2:482, 1981; by the homology alignment algorithm of Needleman and Wunsch, J. Mol. Biol. 48:443, 1970; by the search for similarity method of Pearson and Lipman, Proc. Natl. Acad. Sci. USA 85:2444, 1988; preferably by computerized implementations of these algorithms (GAP, BESTFIT, FASTA, and TFASTA) in the Wisconsin Genetics Software Package Release 7.0, Genetics Computer Group, 575 Science Dr., Madison, Wis. The reference nucleic acid may be a full-length molecule or a portion of a longer molecule. Alternatively, two nucleic acids are have substantial identity if one hybridizes to the other under stringent conditions, as described below.

A first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate constructs. Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence which is annealed to a DNA template to initiate the polymerase chain reaction.

"Transformed," "transfected," or "transgenic" refers to a cell, tissue, organ, or organism into which has been introduced a foreign nucleic acid, such as a recombinant construct. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or construct.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g. rRNA, tRNA); and other types of gene function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element which may also be a component or part of an expression construct. Examples of genetic components include, but are not limited to promoter regions, 5' untranslated leaders, introns, genes, 3' untranslated regions, and other regulatory sequences or sequences which affect transcription or translation of one or more nucleic acid sequences.

The term "DNA construct" refers to a DNA molecule capable of plant genomic integration, comprising one or more transgene DNA sequences that have been linked in a functionally operative manner using well-known recombinant DNA techniques. A "plurality" of DNA constructs refers to two or more.

"Complementary" refers to the natural association of nucleic acid sequences by base-pairing (A-G-T pairs with the complementary sequence T-C-A). Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of percent nucleotide or amino acid positional identity, respectively, i.e., sequence similarity or identity. Homology also refers to the concept of similar functional properties among different nucleic acids or proteins.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, organ, or cell type, a promoter may display "enhanced" expression, i.e., a higher level of expression, in one part (e.g., cell type, tissue, or organ) of the plant compared to other parts of the plant. Temporally regulated promoters are functional only or predominantly during certain period of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Suitable expression constructs for introducing exogenous DNA into plant cells are well known to those of skill in the art. They would include, but are not limited to, disarmed Ti-plasmids for *Agrobacterium*-mediated methods. These constructs can contain a resistance marker (although usually not necessary to the practice of the present invention in addition to the herbicide resistance coding sequence), one or more T-DNA borders, and origins of replication for *E. coli* and *Agrobacterium* along with one or more genes of interest and associated regulatory regions. Those of skill in the art are aware that for *Agrobacterium*-mediated transformation a number of strains and methods are available. Such strains would include but are not limited to *Agrobacterium* strains C58, LBA4404, EHA101 and EHA105. Particularly preferred strains are *Agrobacterium tumefaciens* strains.

Several methods are available for introducing DNA sequences into plant cells and are well known in the art. Suitable methods include but are not limited to bacterial infection (e.g., with *Agrobacterium* as described above), binary bacterial artificial chromosome constructs, direct delivery of DNA (e.g. via PEG-mediated transformation, desiccation/inhibition-mediated DNA uptake, electroporation, agitation with silicon carbide fibers), and acceleration of DNA coated particles (reviewed in Potrykus, Ann. Rev. Plant Physiol. Plant Mol. Biol., 42: 205, 1991).

Methods for specifically transforming dicots primarily use *Agrobacterium tumefaciens*. For example, transgenic plants reported include but are not limited to cotton (U.S. Pat. No. 5,004,863; U.S. Pat. No. 5,159,135; U.S. Pat. No. 5,518,908, WO 97/43430), soybean (U.S. Pat. No. 5,569,834; U.S. Pat. No. 5,416,011; McCabe et al., Bio/Technology, 6:923, 1988; Christou et al., Plant Physiol., 87:671, 1988); Brassica (U.S. Pat. No. 5,463,174), and peanut (Cheng et al., Plant Cell Rep., 15: 653, 1996).

Similar methods have been reported in the transformation of monocots. Transformation and plant regeneration using these methods have been described for a number of crops including but not limited to asparagus (*Asparagus officinalis*; Bytebier et al., Proc. Natl. Acad. Sci. U.S.A., 84: 5345, 1987); barley (*Hordeum vulgarae*; Wan and Lemaux, Plant Physiol., 104: 37, 1994); maize (*Zea mays*; Rhodes, C. A., et al., Science, 240: 204, 1988; Gordon-Kamm, et al., Plant Cell, 2: 603, 1990; Fromm, et al., Bio/Technology, 8: 833, 1990; Koziel, et al., Bio/Technology, 11: 194, 1993); oats (*Avena saliva*; Somers, et al., Bio/Technology, 10: 1589, 1992); orchardgrass (*Dactylis glomerata*; Horn, et al., Plant Cell Rep., 7: 469, 1988); rice (*Oryza sativa*, including indica and japonica varieties, Toriyama, et al., Bio/Technology, 6: 10, 1988; Zhang, et al., Plant Cell Rep., 7: 379, 1988; Luo and Wu, Plant Mol. Biol. Rep., 6: 165, 1988; Zhang and Wu, Theor. Appl. Genet., 76: 835, 1988; Christou, et al., Bio/Technology, 9: 957, 1991); sorghum (*Sorghum bicolor*; Casas, A. M., et al., Proc. Natl. Acad. Sci. U.S.A., 90: 11212, 1993); sugar cane (*Saccharum* spp.; Bower and Birch, Plant J., 2: 409, 1992); tall fescue (*Festuca arundinacea*; Wang, Z. Y. et al., Bio/Technology, 10: 691, 1992); turfgrass (*Agrostis palustris*; Zhong et al., Plant Cell Rep., 13: 1, 1993); wheat (*Triticum aestivum*; Vasil et al., Bio/Technology, 10: 667, 1992; Weeks T., et al., Plant Physiol., 102: 1077, 1993; Becker, et al., Plant, J. 5: 299, 1994), and alfalfa (Masoud, S. A., et al., Transgen. Res., 5: 313, 1996). It is apparent to those of skill in the art that a number of transformation methodologies can be used and modified for production of stable transgenic plants from any number of target crops of interest.

Exemplary nucleic acids which may be introduced by the methods encompassed by the present invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, or structure as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

N-phosphonomethylglycine, also known as glyphosate, is a well known herbicide that has activity on a broad spectrum of plant species. Glyphosate is the active ingredient of Roundup® (Monsanto Co.), a safe herbicide having a desirably short half life in the environment. When applied onto a plant surface, glyphosate moves systemically through the plant. Glyphosate is toxic to plants by inhibiting the shikimic acid pathway that provides a precursor for the synthesis of aromatic amino acids. Specifically, glyphosate affects the conversion of phosphoenolpyruvate and 3-phosphoshikimic acid to 5-enolpyruvyl-3-phosphoshikimic acid by inhibiting the enzyme 5-enolpyruvyl-3-phosphoshikimate synthase (hereinafter referred to as EPSP synthase or EPSPS). For purposes of the present invention, the term "glyphosate" should be considered to include any herbicidally effective form of N-phosphomethylglycine (including any salt thereof) and other forms that result in the production of the glyphosate anion in planta.

Through plant generic engineering methods, it is possible to produce glyphosate tolerant plants by inserting into the plant genome a DNA molecule that causes the production of higher levels of wild-type EPSPS (Shah et al., Science 33:478-481 (1986). Glyphosate tolerance can also be achieved by the expression of EPSPS variants that have lower affinity for glyphosate and therefore retain their catalytic activity in the presence of glyphosate (U.S. Pat. No. 4,535,060) or the expression of EPSPS genes isolated from organisms resistant to glyphosate activity (U.S. Pat. No. 5,633,435). Variants of the wild-type EPSPS enzyme have been isolated that are glyphosate-resistant as a result of alterations in the EPSPS amino acid coding sequence (Kishore et al., Annu. Rev. Biochem. 57:627-663 (1988); Schulz et al., Arch. Microbiol. 137:121-123 (1984); Sost et al., FEBS Lett. 173: 238-241 (1984); Kishore et al., In "Biotechnology for Crop Protection" ACS Symposium Series No. 379. Eds. Hedlin et al., 37-48 (1988). Enzymes that degrade glyphosate in the plant tissues (U.S. Pat. No. 5,463,175) are also capable of conferring cellular tolerance to glyphosate. Such genes, therefore, allow for the production of transgenic crops that are tolerant to glyphosate, thereby allowing glyphosate to be used for effective weed control with minimal concern of crop damage. For example, glyphosate tolerance has been genetically engineered into corn (U.S. Pat. No. 5,554,798), wheat (Zhou et al. Plant Cell Rep. 15:159-163, (1995), soybean (WO 9200377) and canola (WO 9204449).

Glyphosate Spray Tests

In one embodiment, a growth chamber, greenhouse, or field evaluation for glyphosate tolerance is conducted. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion). Illustratively, water-soluble glyphosate salts useful herein are disclosed in U.S. Pat. No. 3,799,758 and U.S. Pat. No. 4,405,531 to Franz, the disclosure of which is incorporated herein by reference. Glyphosate salts that can be used according to the present invention include but are not restricted to alkali metal, for example sodium and potassium, salts; ammonium salt; $C_{1-16}$ alkylammonium, for example dimethylammonium and isopropylammonium, salts; $C_{1-16}$ alkanolammonium, for example monoethanolammonium, salt; $C_{1-16}$ alkylsulfonium, for example trimethylsulfonium, salts; mixtures thereof and the like. The glyphosate acid molecule has three acid sites having different pKa values; accordingly mono-, di- and tribasic salts, or any mixture thereof, or salts of any intermediate level of neutralization, can be used.

Glyphosate salts are commercially significant in part because they are water-soluble. Many ammonium, alkylammonium, alkanolammonium, alkylsulfonium and alkali metal salts are highly water-soluble, allowing for formulation as highly concentrated aqueous solutions which can be diluted in water at the point of use.

Such concentrated aqueous solutions can contain about 50 to about 500 grams per liter of glyphosate, expressed as acid equivalent (g a.e./l). Higher glyphosate concentrations, for example about 300 to about 500 g a.e./l, are preferred.

Glyphosate salts are alternatively formulated as water-soluble or water-dispersible compositions, in the form for example of powders, granules, pellets or tablets. Such compositions are often known as dry formulations, although the term "dry" should not be understood in this context to imply the complete absence of water. Typically, dry formulations contain less than about 5% by weight of water, for example about 0.5% to about 2% by weight of water. Such formulations are intended for dissolution or dispersion in water at the point of use.

Contemplated dry glyphosate formulations can contain about 5% to about 80% by weight of glyphosate, expressed as acid equivalent (% a.e.). Higher glyphosate concentrations within the above range, for example about 50% to about 80% a.e., are preferred. Especially useful salts of glyphosate for making dry formulations are sodium and ammonium salts.

Plant treatment compositions and liquid and dry concentrate compositions of the invention can optionally contain one or more desired excipient ingredients. Especially useful excipient ingredients for glyphosate compositions are surfactants, which assist in retention of aqueous spray solutions on the relatively hydrophobic surfaces of plant leaves, as well as helping the glyphosate to penetrate the waxy outer layer (cuticle) of the leaf and thereby contact living tissues within the leaf. Surfactants can perform other useful functions as well.

There is no restriction in the type or chemical class of surfactant that can be used in glyphosate compositions of the invention. Nonionic, anionic, cationic and amphoteric types, or combinations of more than one of these types, are all useful in particular situations. However, it is generally preferred that at least one of the surfactants, if any, present should be other than anionic, i.e., at least one of the surfactants should be nonionic, cationic or amphoteric. Standard reference sources from which one of skill in the art can select suitable surfactants, without limitation to the above mentioned classes, include *Handbook of Industrial Surfactants*, Second Edition (1997) published by Gower, *McCutcheon's Emulsifiers and Detergents*, North American and International Editions (1997) published by MC Publishing Company, and *International Cosmetic Ingredient Dictionary*, Sixth Edition (1995) Volumes 1 and 2, published by the Cosmetic, Toiletry and Fragrance Association.

Examples of commercial formulations of glyphosate include, without restriction, those sold by Monsanto Company as ROUNDUP®, ROUNDUP® ULTRA, ROUNDUP® ULTRAMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

The selection of application rates for a glyphosate formulation that comprise a biologically effective dose is within the skill of the ordinary agricultural technician. One of skill in the art will likewise recognize that individual plant conditions, weather conditions and growing conditions can affect the results achieved in practicing the process of the present invention. Over two decades of glyphosate use and published studies relating to such use have provided abundant information from which a weed control practitioner can select glyphosate application rates that are herbicidally effective on particular species at particular growth stages in particular environmental conditions.

In one embodiment, a glyphosate-containing herbicide is applied to the plant comprising the DNA constructs of the present invention, and the plants are evaluated for vegetative and reproductive tolerance to the glyphosate herbicide. Any formulation of glyphosate can be used for testing plants comprising the DNA constructs of the present invention. For example, a glyphosate composition such as Roundup® Ultra can be used. The testing parameters for an evaluation of the glyphosate tolerance of the plant will vary depending on a number of factors. Factors would include, but are not limited to the type of glyphosate formulation, the concentration and amount of glyphosate used in the formulation, the type of plant, the plant developmental stage during the time of the application, environmental conditions, the application method, and the number of times a particular formulation is applied. For example, plants can be tested in a greenhouse environment using a spray application method. The testing range using Roundup® Ultra can include, but is not limited to 8 oz/acre to 256 oz/acre. The preferred commercially effective range can be from 16 oz/acre to 64 oz/acre of Roundup® Ultra, depending on the crop and stage of plant development. A crop can be sprayed with at least one application of a glyphosate formulation. For testing in cotton, an application of 32 oz/acre at the 3-leaf stage may be followed by additional applications at later stages in development. For wheat, an application of 32 oz/acre of Roundup® Ultra at the 3-5 leaf stage can be used and may be followed with a pre- or post-harvest application, depending on the type of wheat to be tested. The test parameters can be optimized for each crop in order to find the particular plant comprising the constructs of the present invention that confers the desired commercially effective glyphosate tolerance level.

The present method for selecting DNA constructs in a model plant can be applied to selecting DNA constructs that are useful for producing male or female sterile transgenic crop plants and their use in the production of hybrid seed, including hybrid seed with restored fertility. Thus, relating to an additional embodiment of the present invention, there is provided a method of producing hybrid seed of a crop plant that comprises first regenerating a crop plant from a transformed crop plant cell that contains a DNA construct selected by the method of the present invention. The method being applied to select a DNA construct wherein the transgenic model plant is vegetatively tolerant to a herbicide and reproductively sterile, preferably male sterile. In this preferred embodiment, the method provides a DNA construct which when incorporated in a transgenic crop plant will result in plants that are, when exposed to glyphosate, produce male sterile, female fertile plants. During production of hybrid seed, this transgenic crop plant serves as the seed parent plant and is sprayed with glyphosate and rendered male sterile, but remains female fertile and is pollinated by the pollen from a male fertile parent plant.

The following examples are included to demonstrate preferred embodiments of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention, therefore all matter set forth or shown in the accompanying drawings is to be interpreted as illustrative and not in a limiting sense.

Example 1

Genetic Elements of the DNA Constructs

The DNA constructs used are either pUC cloning constructs or double border plant transformation constructs that contain DNA segments that provide replication function and antibiotic selection in bacterial cells, for example, an *E. coli* origin of replication such as ori322, a broad host range origin of replication such as oriV or oriRi, and a coding region for a selectable marker such as Spc/Str that encodes for Tn7 aminoglycoside adenyltransferase (aadA) confers resistance to spectinomycin or streptomycin, or a gentamicin (Gm, Gent) selectable marker. For plant transformation, the host bacterial strain is *Agrobacterium tumefaciens* ABI or LBA4404.

The genetic elements of the DNA constructs are assembled to have in operable linkage a promoter that functions in plants, a herbicide tolerance encoding polynucleotide sequence, and a 3' termination region. DNA constructs used in the method of the current invention comprise any promoter known to function to cause the transcription in plant cells and any herbicide tolerance encoding polynucleotide sequence known to confer herbicide tolerance to plant cells. The herbicide tolerance polynucleotide sequences include, but are not limited to polynucleotide sequences encoding for proteins involved in herbicide tolerance encoding for 5-enolpyruvylshikimate-3-phosphate synthase (EPSPS, described in U.S. Pat. Nos. 5,627,061, and 5,633,435, herein incorporated by reference in its entirety; Padgette et al. (1996) *Herbicide Resistant Crops*, Lewis Publishers, 53-85, and in Penaloza-Vazquez, et al. (1995) *Plant Cell Reports* 14:482-487) and aroA (U.S. Pat. No. 5,094,945) for glyphosate tolerance, bromoxynil nitrilase (Bxn) for Bromoxynil tolerance (U.S. Pat. No. 4,810,648), phytoene desaturase (crtI (Misawa et al, (1993) *Plant Journal* 4:833-840, and (1994) *Plant Jour* 6:481-489) for tolerance to norflurazon, acetobydroxyacid synthase (AHAS, Sathasilvan et al. (1990) *Nucl. Acids Res.* 18:2188-2193) and the bar gene for tolerance to glufosinate (DeBlock, et al. (1987) *EMBO J.* 6:2513-2519. Herbicides for which transgenic plant tolerance has been demonstrated and the method of the present invention can be applied include, but are not limited to: glyphosate, glufosinate, sulfonylureas, imidazolinones, bromoxynil, delapon, cyclohezanedione, protoporphyrionogen oxidase inhibitors, and isoxaslutole herbicides.

Genetic elements of transgene DNA constructs used for plant transformation and expression of transgenes in plants include, but are not limited to: the P-CaMV.35S promoter (U.S. Pat. No. 5,858,742, herein incorporated by reference in its entirety), for example, the enhanced P-CaMV.35S from Cauliflower mosaic virus containing a duplication of the -90-300 region as described in U.S. Pat. No. 5,424,200, herein incorporated by reference in its entirety; the Figwort mosaic virus promoter, P-FMV, as described in U.S. Pat. No. 5,378,619, herein incorporated by reference in its entirety, the P-AtEF1a (P-AtEF1 or a EF1a) a promoter region from the *Arabidopsis thaliana* elongation factor gene 1a; the Gbox10 and Gbox11motif (Fumiharu et al., (1999) Plant J. 18:443-448); the DC3 promoter region from carrot (Seffens et al., Develop. Genet. 11:65-76); the TP12 promoter (GenBank accession no. U68483); DNA molecules encoding plastid transit peptides, for example, the *Arabidopsis* EPSPS chloroplast transit peptide, At.CTP2 as described in U.S. Pat. No. 5,633,435, herein incorporated by reference in its entirety. The method of the present invention enables one of skill in the art of plant molecular biology to design and assemble plant expression cassettes that contain promoters of known and unknown function. The genetic elements of the DNA construct further comprise 5' leader polynucleotides for example, the Hsp70 non-translated leader sequence from *Petunia hybrida* as described in U.S. Pat. No. 5,362,865, herein incorporated by reference in its entirety.

The genetic elements further comprise herbicide tolerance genes that include, but are not limited to, for example, the aioA:CP4 coding region for EPSPS glyphosate resistant enzyme isolated from *Agrobacterium tumefaciens* (AGRTU) strain CP4 as described in U.S. Pat. No. 5,633,435, herein incorporated by reference in its entirety. The genetic elements of the DNA construct further comprise termination regions that include, but are not limited to, the E9 3' termination region the pea RbcS gene that functions as a polyadenylation signal; the nos is the 3' end of the nopaline synthase gene that functions as a polyadenylation signal. The generic elements of the DNA construct further comprise the right border (RB) and left borders (LB) of the Ti plasmid of *Agrobacterium tumefaciens* octopine and nopaline strains.

Example 2

Model Plant Transformation Methods

*Arabidopsis* Transformation by Vacuum Infiltration

*Arabidopsis* embryos have been transformed by an *Agrobacterium* mediated method described by Bechtold N, et al., CR Acad Sci Paris Sciences di la vie/life sciences 316: 1194-1199, (1993). This method has been modified for use with the constructs of the present invention to provide a rapid and efficient method to transform *Arabidopsis* and select for a herbicide tolerant phenotype An *Agrobacterium* strain ABI containing a DNA construct is prepared as inoculum by growing in a culture tube containing 10 mls Luria Broth and antibiotics, for example, 1 ml/L each of spectinomycin (100 mg/ml), chloramphenicol (25 mg/ml), kanamycin (50 mg/ml) or the appropriate antibiotics as determined by those skilled in the art. The culture is shaken in the dark at 28° C. for approximately 16-20 hours.

The *Agrobacterium inoculum* is pelleted by centrifugation and resuspended in 25 ml Infiltration Medium (MS Basal Salts 0.5%, Gamborg's B-5 Vitamins 1%, Sucrose 5%, MES 0.5 g/L, pH 5.7) with 0.44 nM benzylaminopurine (10 ul of a 1.0 mg/L stock in DMSO per liter) and 0.02% Silwet L-77 to an $OD_{600}$ of 0.6.

Mature flowering *Arabidopsis* plants are vacuum infiltrated in a vacuum chamber with the *Agrobacterium inoculum* by inverting the pots containing the plants into the inoculum. The chamber is sealed, a vacuum is applied for several minutes, release the vacuum suddenly, blot the pots to remove excess inoculum, cover pots with plastic domes and place pots in a growth chamber at 21° C. 16 hours light and 70% humidity. Approximately 2 weeks after vacuum infiltration of the inoculum, each plant with a Lawson 511 pollination bag. Approximately 4 weeks post infiltration, withhold water from the plants to permit dry down. Harvest seed approximately 2 weeks after dry down.

The transgenic *Arabidopsis* plants produced by the infiltrated seed embryos are selected from the nontransgenic plants by a germination selection method. The harvested seed is surface sterilized then spread onto the surface of selection media plates containing MS Basal Salts 4.3 g/L, Gamborg'a B-5 (500 X) 2.0 g/L, Sucrose 10 g/L, MES 0.5 g/L, and 8 g/L Phytagar with Carbenicillin 250 mg/L, Cefotaxirne 100 mg/L, and PPM 2 ml/L and appropriate selection agent added as a filter sterilized liquid solution, after autoclaving. The selection agent can be an antibiotic or herbicide, for example kanamycin 60 mg/L, glyphosate 40-60 µM, or bialaphos 10 mg/L are appropriate concentrations to incorporate into the media depending on the DNA construct and the plant expression cassettes contained therein that are used to transform the embryos. When using glyphosate selection, the sucrose is deleted from the basal medium. Put plates into a box in a 4° C. to allow the seeds to vernalize for ~2-4 days. After seeds are vernalized, transfer to a growth chamber with cool white light bulbs at a 16/8 light/dark cycle and a temperature of 23 C. After 5-10 days at ~23° C. and a 16/8 light cycle, the transformed plants will be visible as green plants. After another 1-2 weeks, plants will have at least one set of true leaves. Transfer plants to soil, cover with a germination dome, and move to a growth chamber, keep covered until new growth is apparent, usually 5-7 days.

Micro-Tomato Transformation Method—Glyphosate Selection

Micro-Tom seeds (Ball Seed Co., West Chicago, Ill.) are surface-sterilized by soaking in 25% Chlorox with 1-2 drops of Tween 20 for 10 minutes while stirring frequently. The seeds are then rinsed 3 times with sterile deionized water. The seeds are germinated in phytatrays maintained at 28° C. under the dark for 5 days. The phytatray cultures are transferred and grown at 24° C. under a 16 h photoperiod until the seedlings are open in a very narrow "V" shape to produce cotyledons which are at the appropriate stage for explanting. Typically, the seedlings will be explanted about six days after germination.

One day before *Agrobacterium*-mediated transformation, a loopful of the *Agrobacterium bacterium* cells transformed with the a DNA construct containing a glyphosate tolerance plant expression cassette is transferred from a plate culture and inoculated into 2 ml of Luria Broth+antibiotics in a 17×100 Falcon tube, and grown at about 28° C. on a rotator at the speed between medium to high for about 16 hours. Approximately 0.2 ml of the liquid bacterium culture is inoculated into 2 ml of Luria Broth+0.2 mM acetosyringone in a 17×100 mm Falcon tube, and grown at about 28° C. on a rotator at the speed between medium to high for 4 hours. An $O.D._{600}=0.1$ is the desired density for the *Agrobacterium inoculum* for use in the inoculation of the explants.

Micro-Tom cotyledon are excised from the narrow "V" shaped seedlings to make the explants for inoculation. About 50 cotyledon explants are prepared by bathing them in 6 ml of TXD liquid medium and trimming them at both ends using a #15 feather scapel blade. Immediately after the trimming, the 50 cotyledon explants are gently placed on "feeder plates". The "feeder plates" are made by overlaying 2 ml of tobacco suspension cells and a sterile filter paper on the plates containing UC2PC medium. The cotyledon explants are gently poked with a sharp forcep (ASIM5311, Stainless French), making six to ten pokes per explant cotyledon. Immediately after poking, the explants are inoculated with 3 ml of *Agrobacterium inoculum* by pipetting the inoculum on to explants. The plates are incubated for 10 minutes at room temperature and the *Agrobacterium inoculum* is then aspirated off with a sterile pipette. The explants are then co-cultured for 2 days at 23-24° C., 16 h photoperiod in plastic bags.

Two days after inoculation the explants are transferred to delay medium, which is an MS based, medium that is supplemented after autoclaving with 500 mg/L carbenicillin, 100 mg/L cefotaxime, 0.1 mg/L IAA, and 2 mg/L zeatin riboside (Biosynth), at a density of 12-16 explants per plate for 7 days at 23-24° C., 16 h photoperiod.

Explants are transferred to shoot induction medium supplemented after autoclaving with 500 mg/L carbenicillin, 100 mg/L cefotaxime, 0.1 mg/L IAA, and 2 mg/L zeatin riboside (Biosynth), and 0.03 mM glyphosate, at a density of 9 explants per plate. All culture plates are placed inside a plastic bag and cultured at 23-24° C., 16 h photoperiod Three to four weeks after transfer of explants to shoot induction medium, the explants form callus and small buds. Explants with callus and/or small buds are separated and transferred to shoot elongation medium (CPE1) that is supplemented after autoclaving with 500 mg/L carbenicillin, 100 mg/L cefotaxime, 0.1 mg/L IAA, and 0.5 mg/L zeatin riboside (Biosynth), and 0.03 mM glyphosate, at a density of 5 explants per plate. They are cultured for three to four weeks, for shoot elongation. All plates are cultured in plastic bags, at 23-24° C., 16 h photoperiod.

When shoots elongate (about 2 to 3 cm in length) they are excised from explants, and transferred to rooting medium, that has been supplemented after autoclaving with 500 mg/L carbenicillin, 75 mg/L cefotaxime, and 1 mg/L IBA, at a density of two to three shoots per plate for three to four weeks. Ten to twelve culture plates are placed in a plastic bag and cultured at 23-24° C., 16 h photoperiod.

| Component | Amount to Add |
|---|---|
| Micro Tom Selection Medium Basal Recipe This medium is used for delay, selection and elongation steps For 1 liter | |
| Gibco MS (500-1117EH) | 4.3 grams |
| Phytotech Gamborg's B5 500X (G219) | 2 ml/L |
| Sucrose (S-5391) | 30 grams |
| Adjust pH to 5.8 with KOH and then add the agar | |
| Sigma TC agar (A-1296) | 10 grams |
| Autoclave for 22 minutes, at 250° F. | |
| Micro Tom Rooting Medium Basal Recipe This medium is used for the rooting medium. For 1 liter | |
| Gibco MS (500-1117EH) | 2.2 grams |
| Phytotech Gamborg's B-5 500X (G219) | 2.0 mls |
| Sucrose (S-5391) | 30 grams |
| Sigma TC agar (A-1296) | 10 grams |
| Autoclave for 22 minutes, at 250° F. | |

Example 3

Crop Plant Transformation Methods

Cotton Transformation

Cotton transformation is performed essentially as described in WO/0036911, herein incorporated by reference in its entirety, or as described in U.S. Pat. No. 5,846,797, herein incorporated by reference in its entirety. A modification of these methods can include but is not limited to the following example. Coker 130 seed is surface sterilized and germinated in the dark. Hypocotyl explants are cut from the germinated seedlings to lengths of about 1-1.5 cm. *Agrobacterium tumefaciens* strain ABI transformed to contain one of the DNA constructs pMON15737, pMON26140, pMON45331, pMON51915, and pMON52060 is grown in Luria broth without antibiotics for 16 hours at 28° C., then diluted to approximately 2×10$^8$ bacteria/ml. The hypotocyl explant is submersed in the *Agro* inoculum for 2-5 minutes, then co-cultivated for about 45 hours on MS+1.9 mg/l KNO3+3% glucose (TRM), 30 explants per plate, 24 C, in the dark. The explants are transferred to TRM containing 150 mg/l cefotaxime and 300 µM glyphosate for four culture periods, each period for approximately six weeks.

Embryogenic calli is segregated from the primary explant at the end of 3$^{rd}$ or 4th culture periods and placed onto same medium. The embryogenic calli are subcultured once by briefly suspending in liquid TRM+3% glucose, followed by pouring suspension onto 'TRM'+150 mg/l cefotaxime+300 µM glyphosate plates. The somatic embryos are harvested 3-8 weeks after the liquid subculture, then grown on Stewart and Hsu media with 0.5% glucose. Plantlets derived from the somatic embryos are matured to about 4-7 cm (3-6 leaves) in Magenta boxes with Stewart & Hsu modified with 40 mM NO3/10 mM NH4+2% sucrose. These plants are then transplanted to potting soil, 4" pots, 100% humidity, 16 hours of light per day, for 4-6 days, followed by 50% humidity 5-10 days.

Tobacco Transformation

Tobacco transformation is performed as follows: stock tobacco plants maintained by in-vitro propagation. Stems are cut into sections and placed into phytatrays. Leaf tissue is cut and placed onto solid pre-culture plates, MS104 to which 2 mls of liquid TXD medium and a sterile Whatman filter disc have been added. Pre-culture the explants in warm room (23° Celsius, continuous light) for 1-2 days. The day before *Agro* inoculation, a 10 µl loop of a transformed *Agrobacterium* containing one of the DNA constructs is placed into a tube containing 10 mls of YEP media with appropriate antibiotics to maintain selection of the DNA construct. The tube is put into a shaker to grow overnight at 28° C. The $OD_{600}$ of the *Agrobacterium* is adjusted to 0.15-0.30 $OD_{600}$ with TXD medium. Inoculate tobacco leaf tissue explants by pipetting 7-8 mls of the liquid *Agrobacterium* suspension directly onto the pre-culture plates covering the explant tissue. Allow the *Agrobacterium* to remain on the plate for 15 minutes. Tilt the plates and aspirate liquid off using a sterile 10 ml wide bore pipette. The explants are co-cultured on these same plates for 2-3 days. The explants are then transferred to MS104 containing these additives, added post autoclaving: 500 mg/L Carb, 100 mg/L Cef, 150 mg/L Van and 300 mg/L Kan. At 3-4 weeks, callus is transferred to fresh Kanamycin medium. At 6-8 weeks shoots should be excised from the callus and cultured on MS0+500 mg/L Carb+100 mg/L Kan media and allowed to root. Rooted shoots are then transferred to soil after 2-3 weeks.

Basal Medium Recipes
MS0
4.4 g MS B-5
30 g Sucrose
9 g Sigma TC agar
MS104
4.4 g MS basal salts+B5 vitamins
30 g Sucrose
1.0 mg BA
0.1 mg NAA
9 g Sigma TC agar
TXD
4.3 g Gibco MS
2 ml Gamborg's B-5 500X
8 ml pCPA (0.5 mg/ml)
0.01 ml Kinetin (0.5 mg/ml)
30 g Sucrose Tomato Transformation The tomato transformation is performed essentially as described in U.S. Pat. No. 5,565,347, herein incorporated by reference in its entirety.

Soybean Transformation Soybean transformation is performed essentially as described in WO 00/42207, herein incorporated by reference in its entirety.

Example 4

Figure 2:
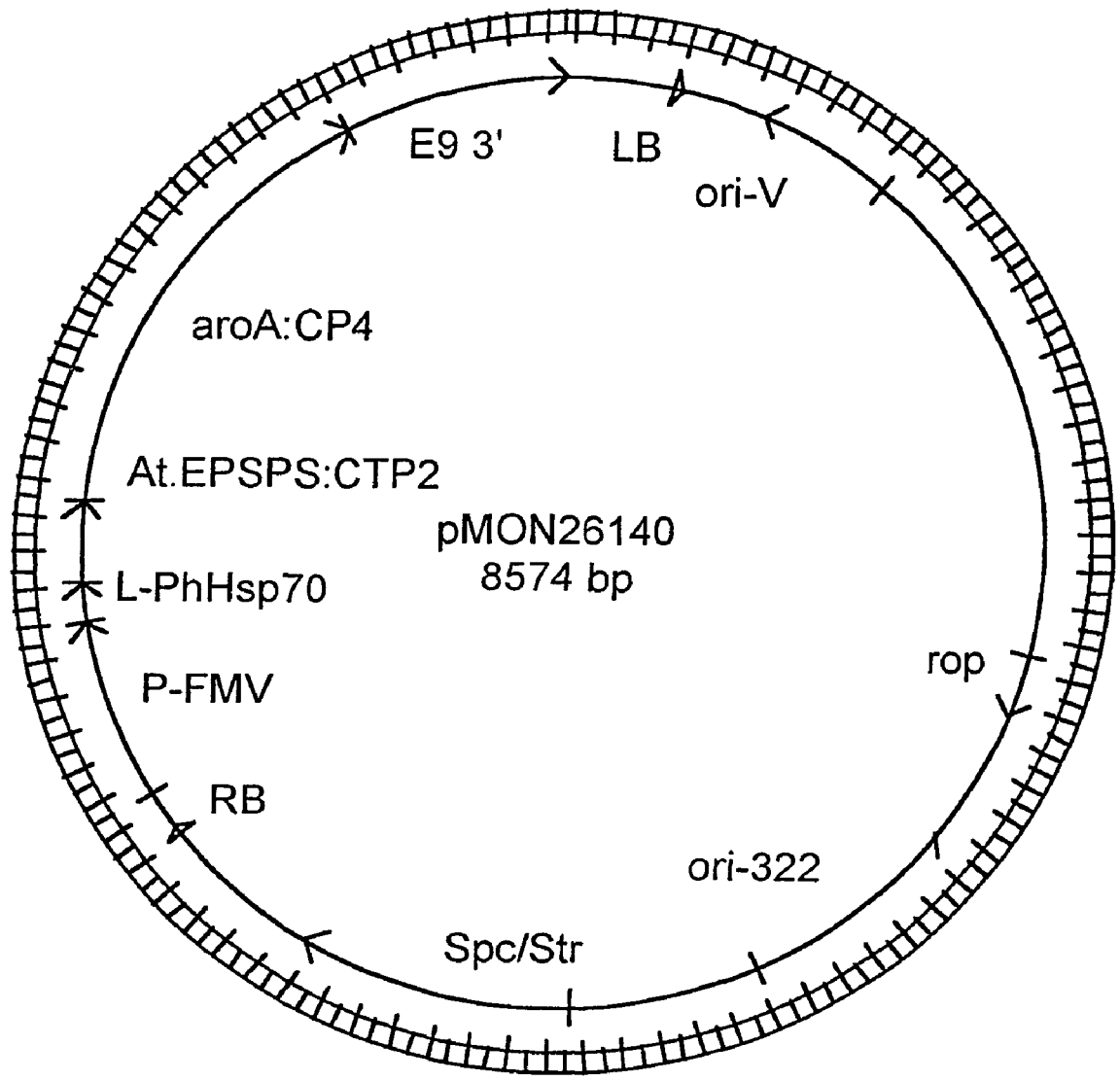
Figure 3:
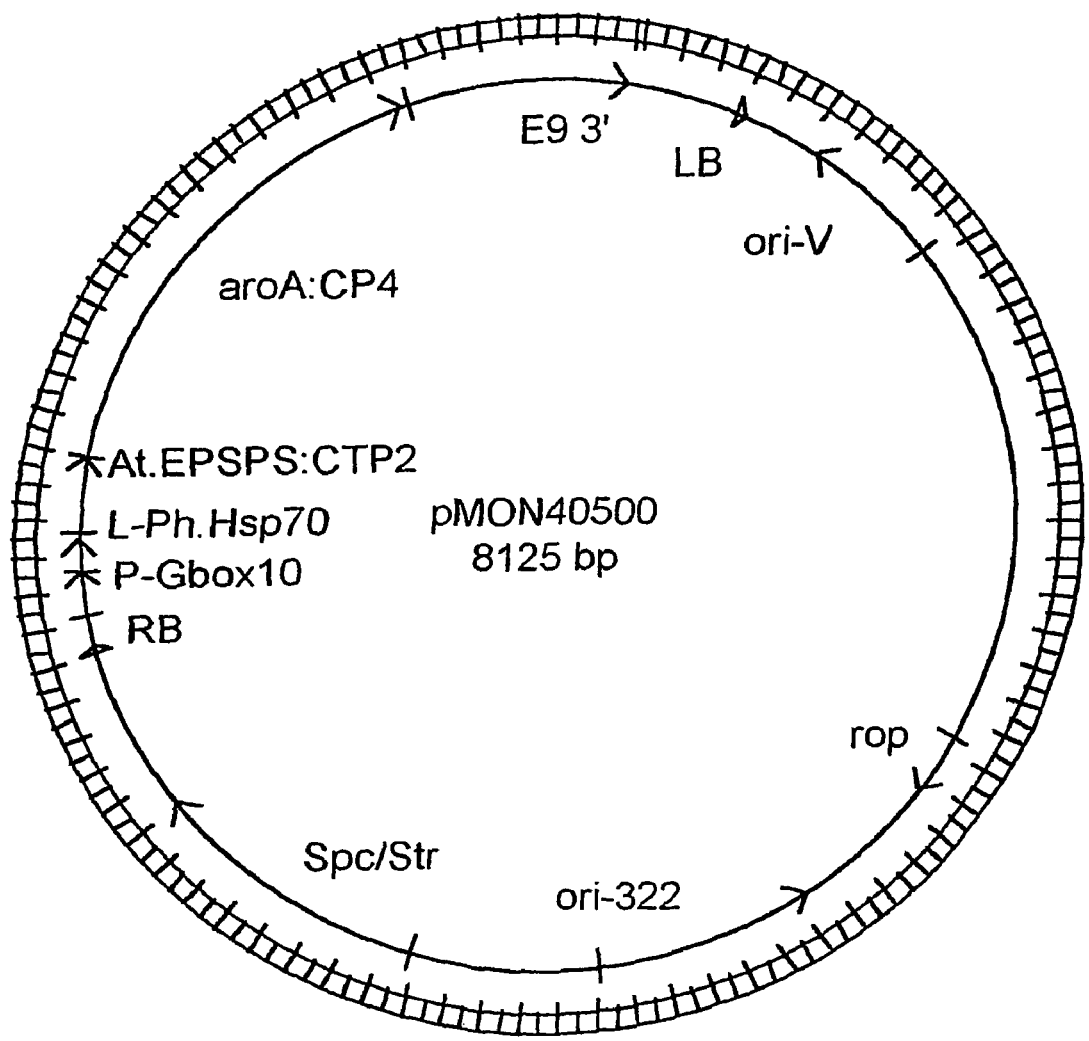
Figure 4:
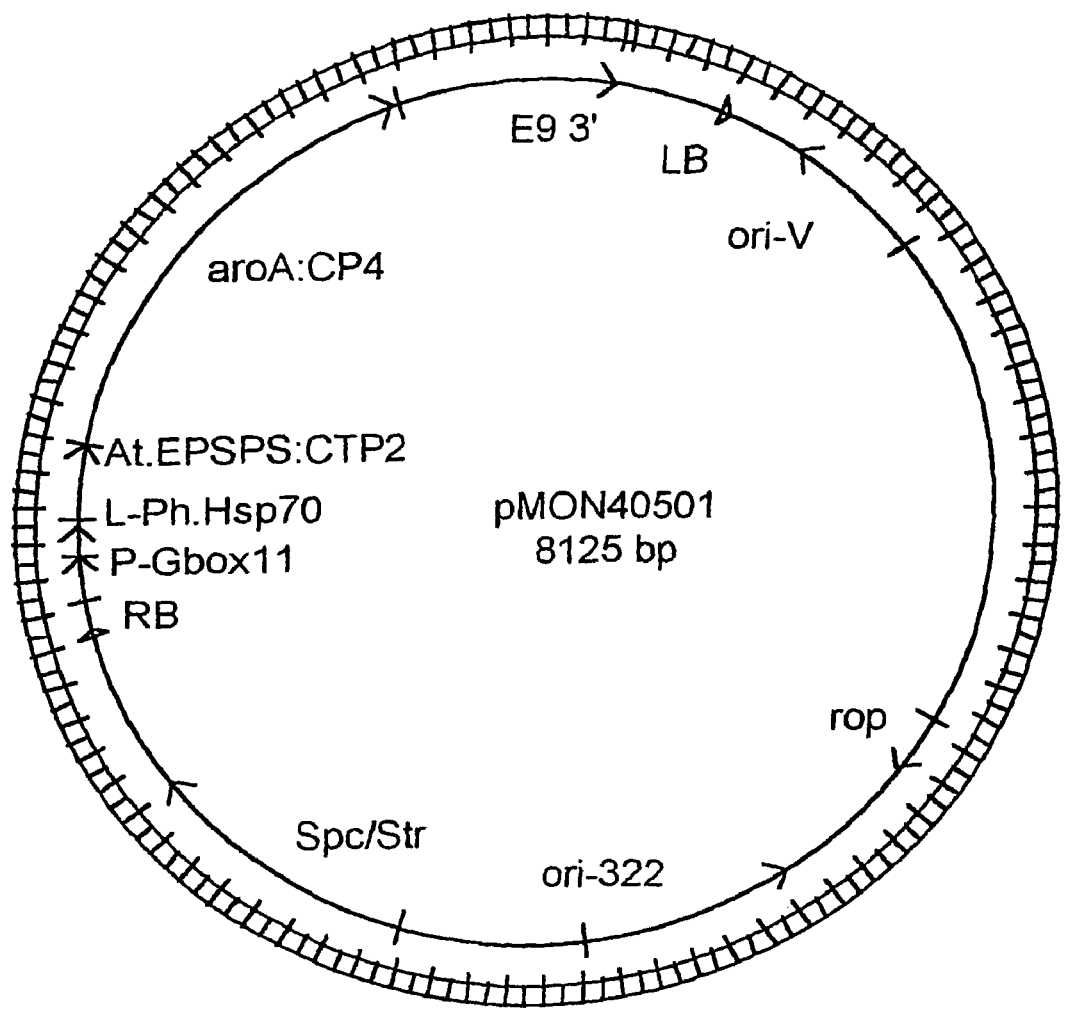
Figure 5:
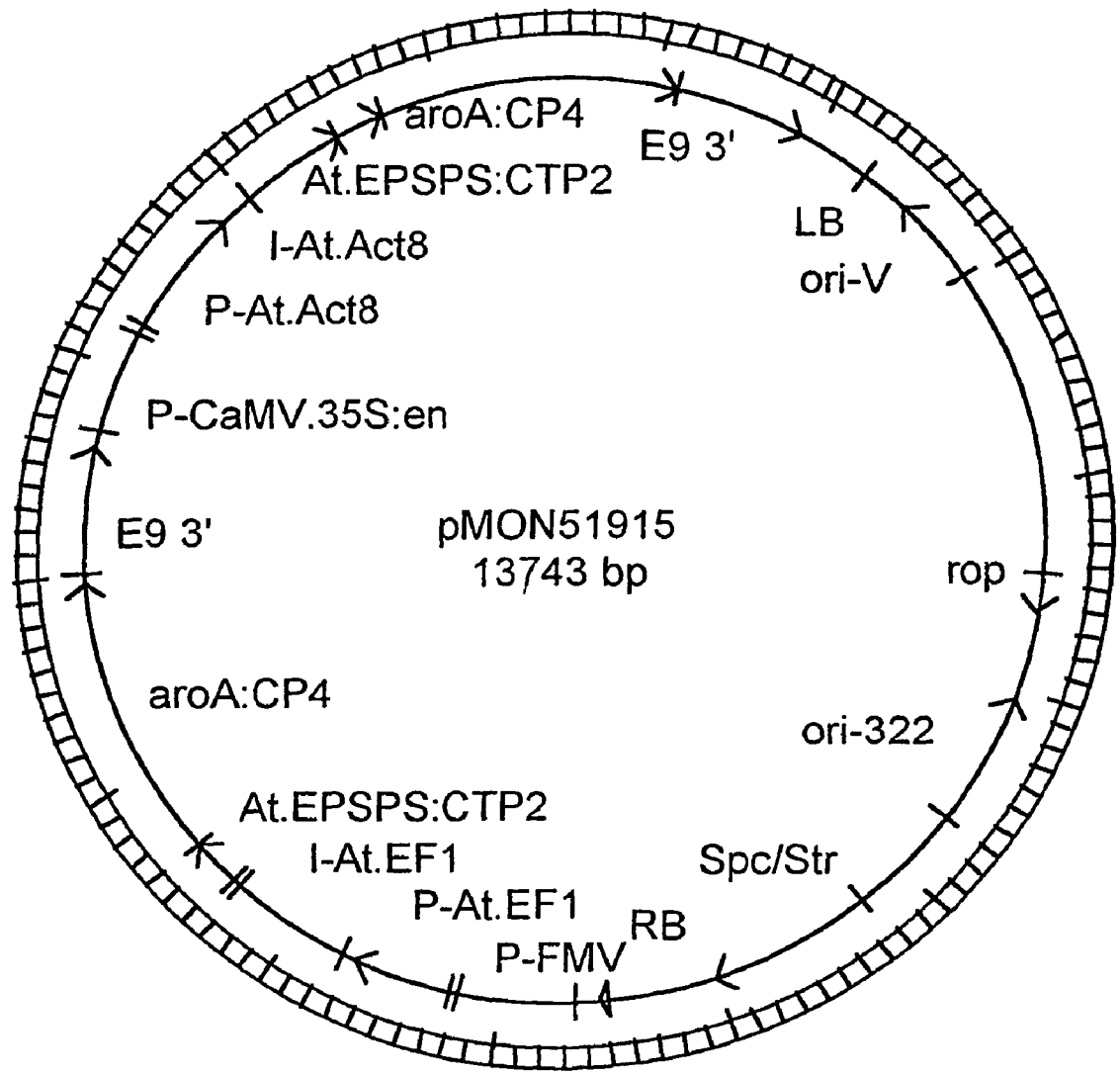
Figure 6:
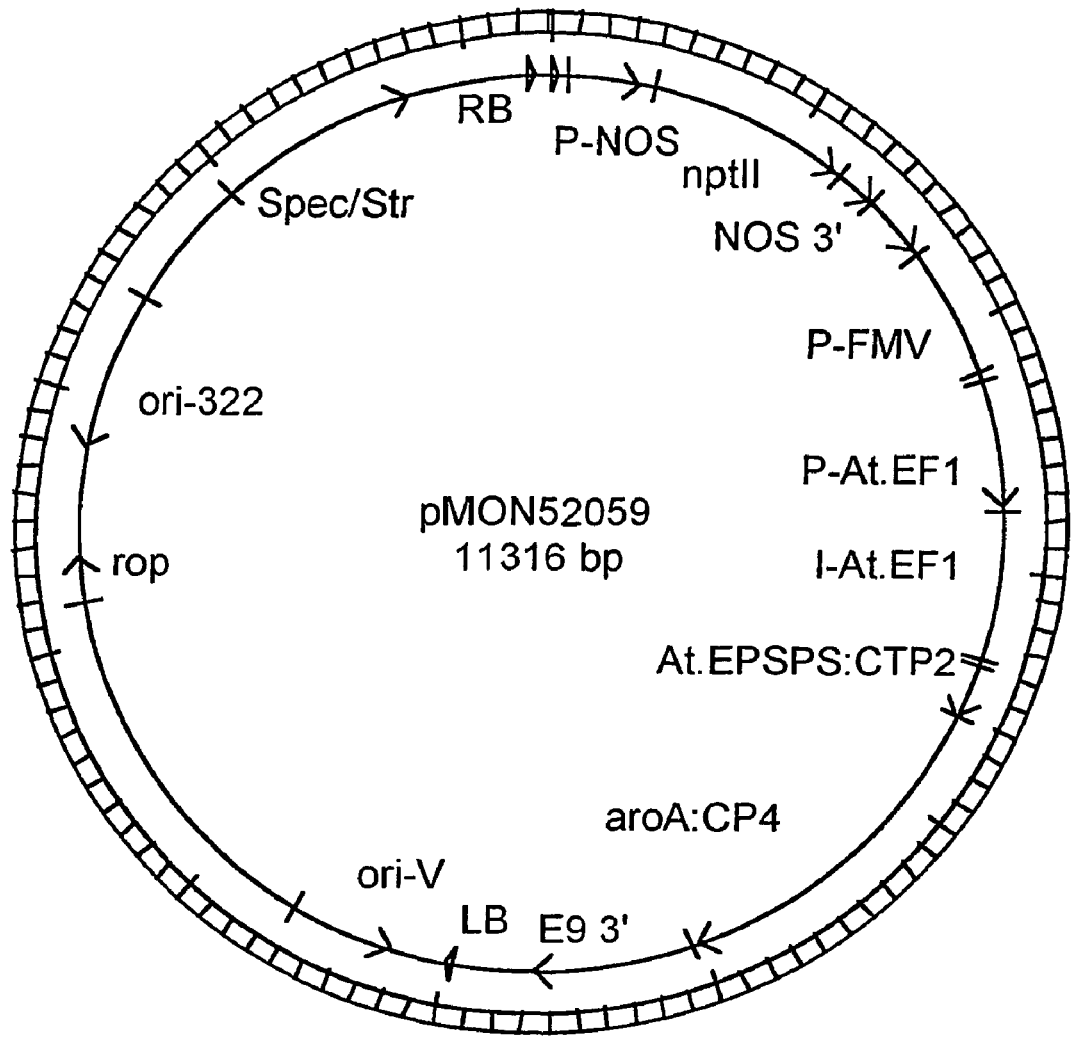
Figure 7:
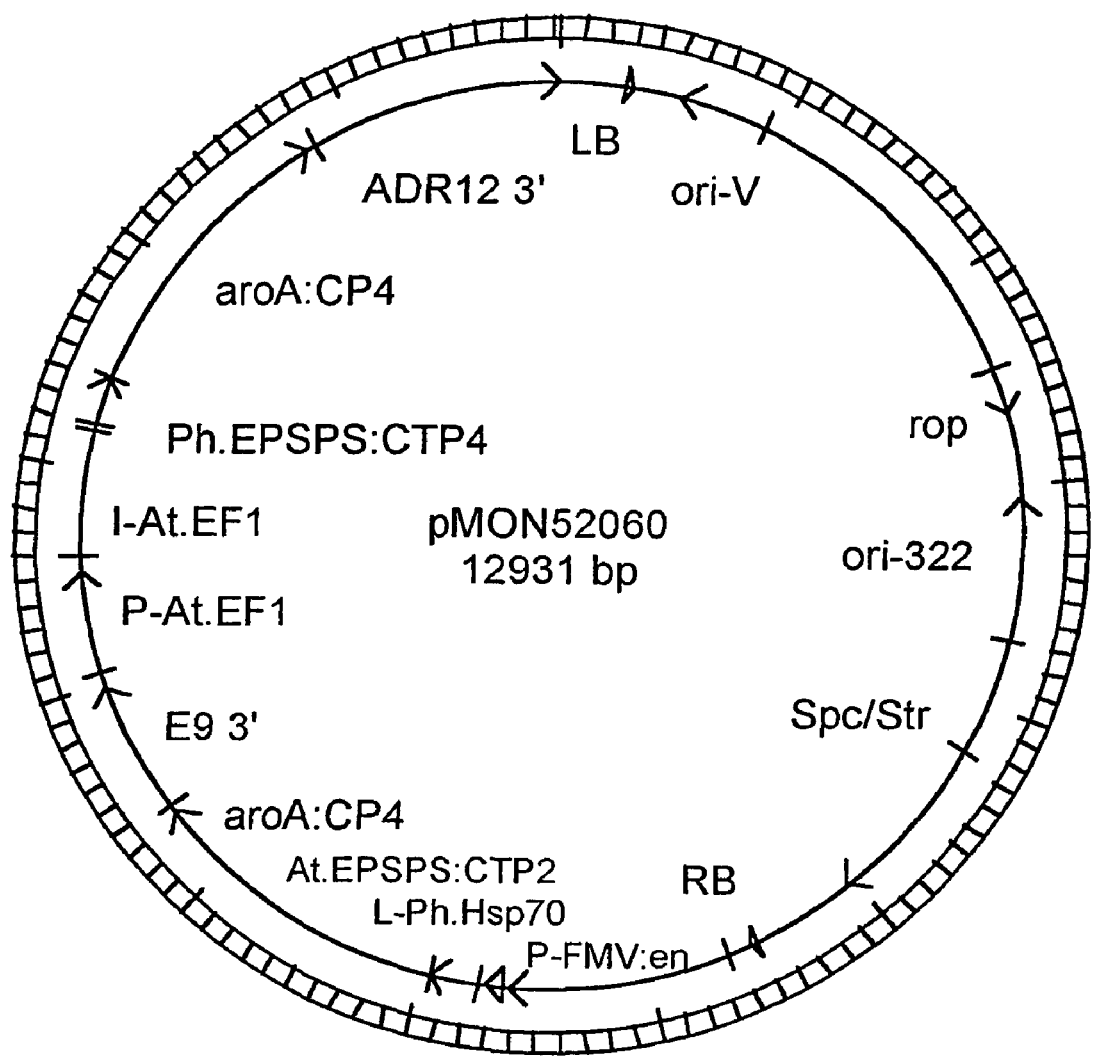
Figure 8:
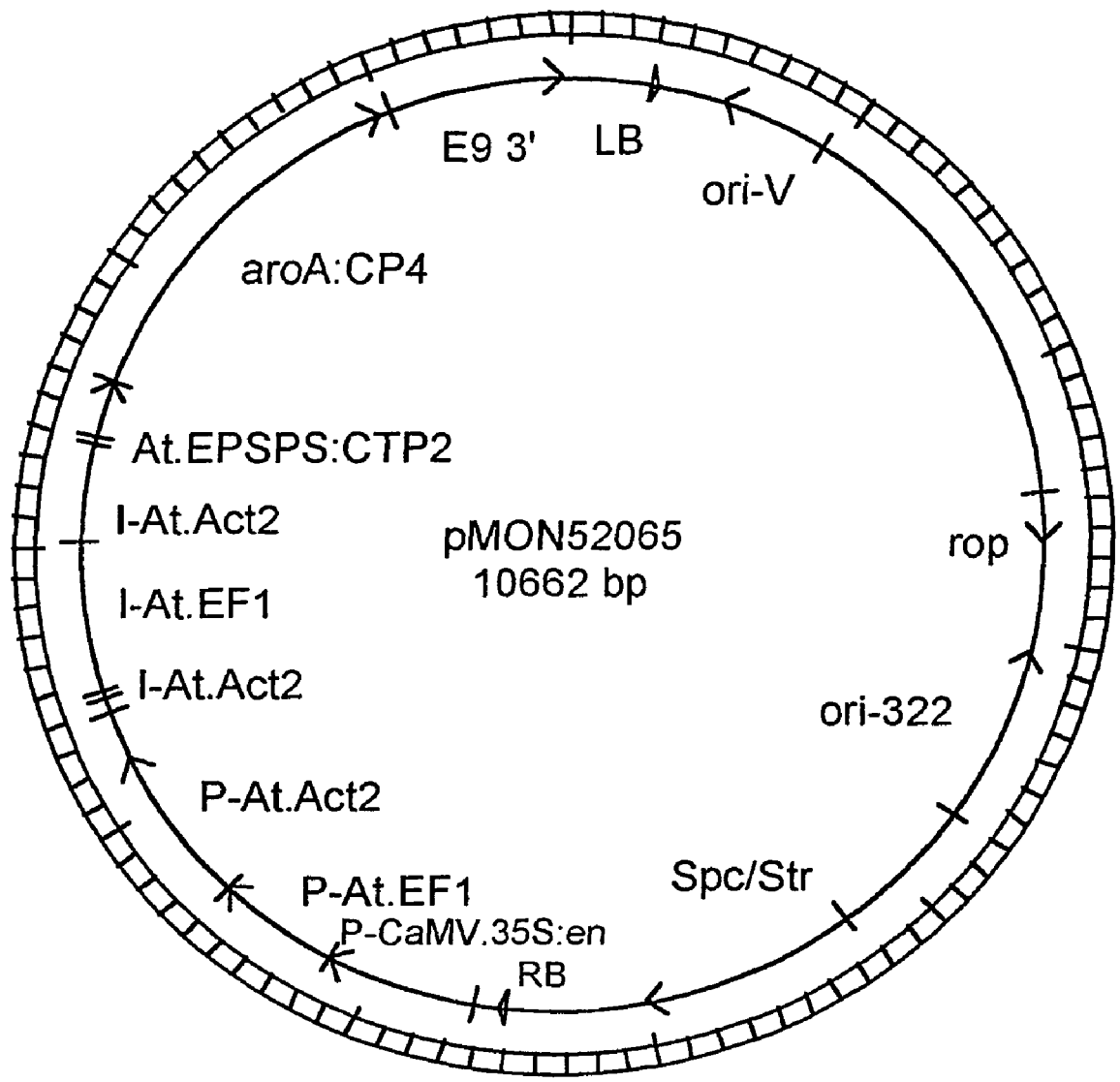
Figure 9:
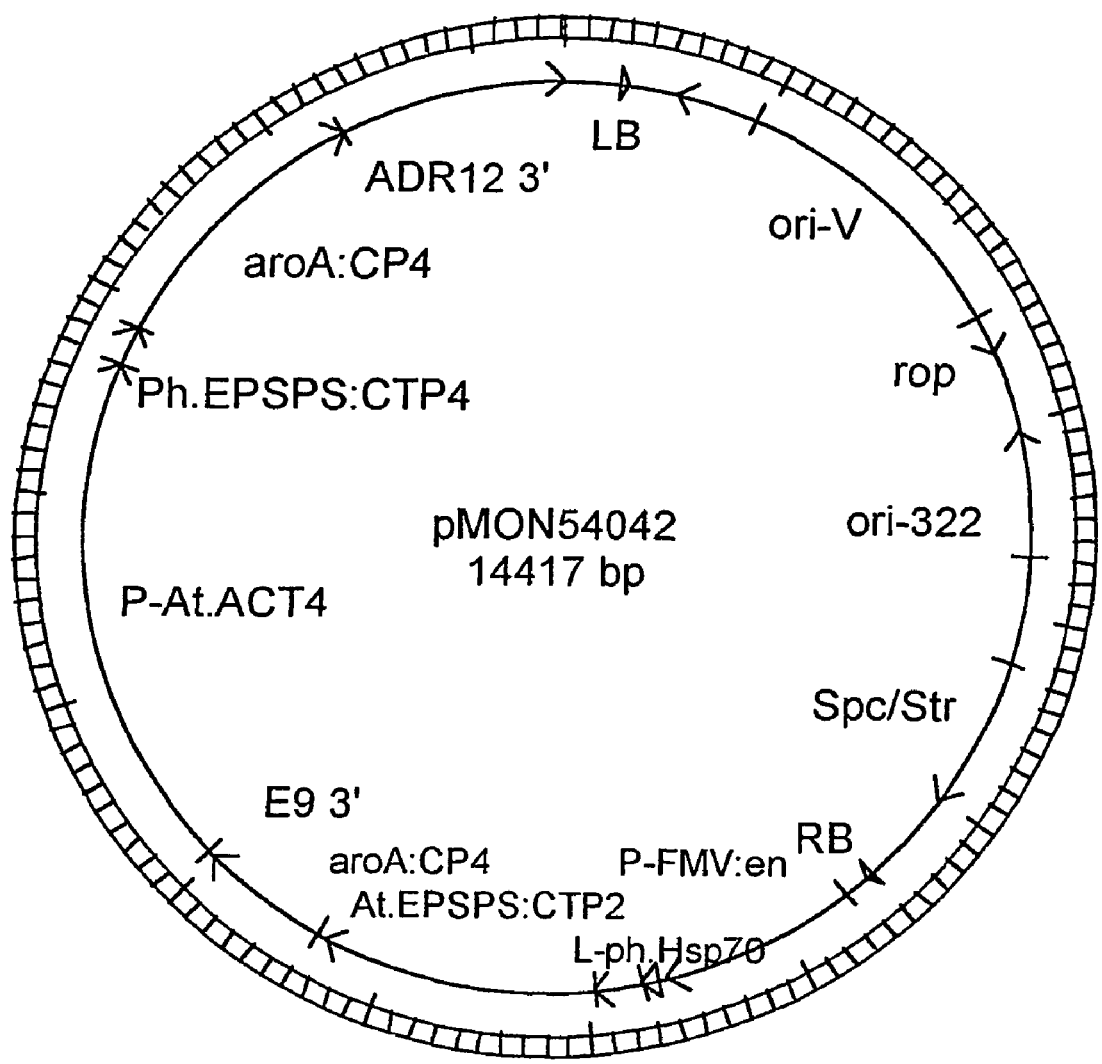
Figure 10:
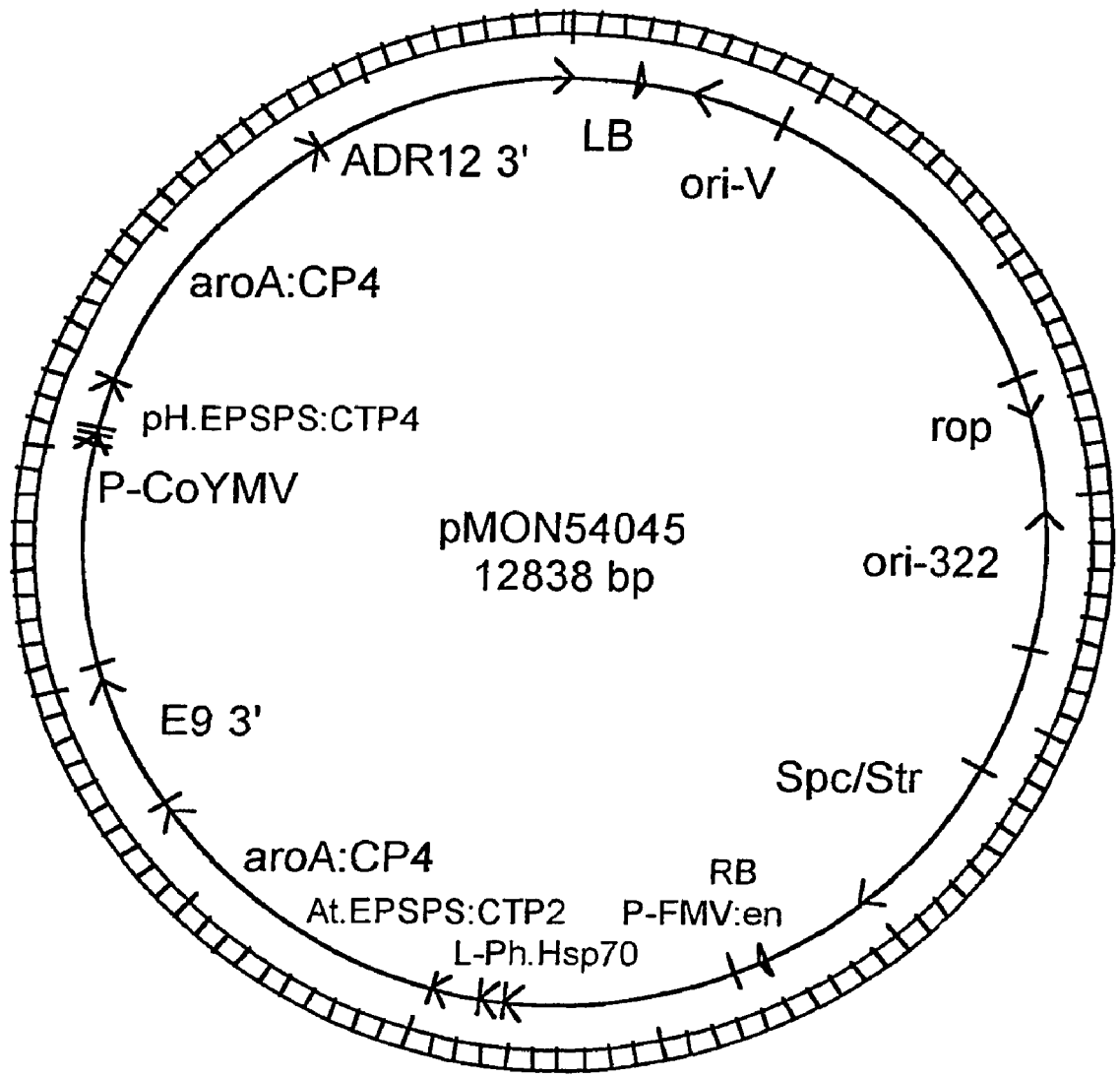
Figure 11:
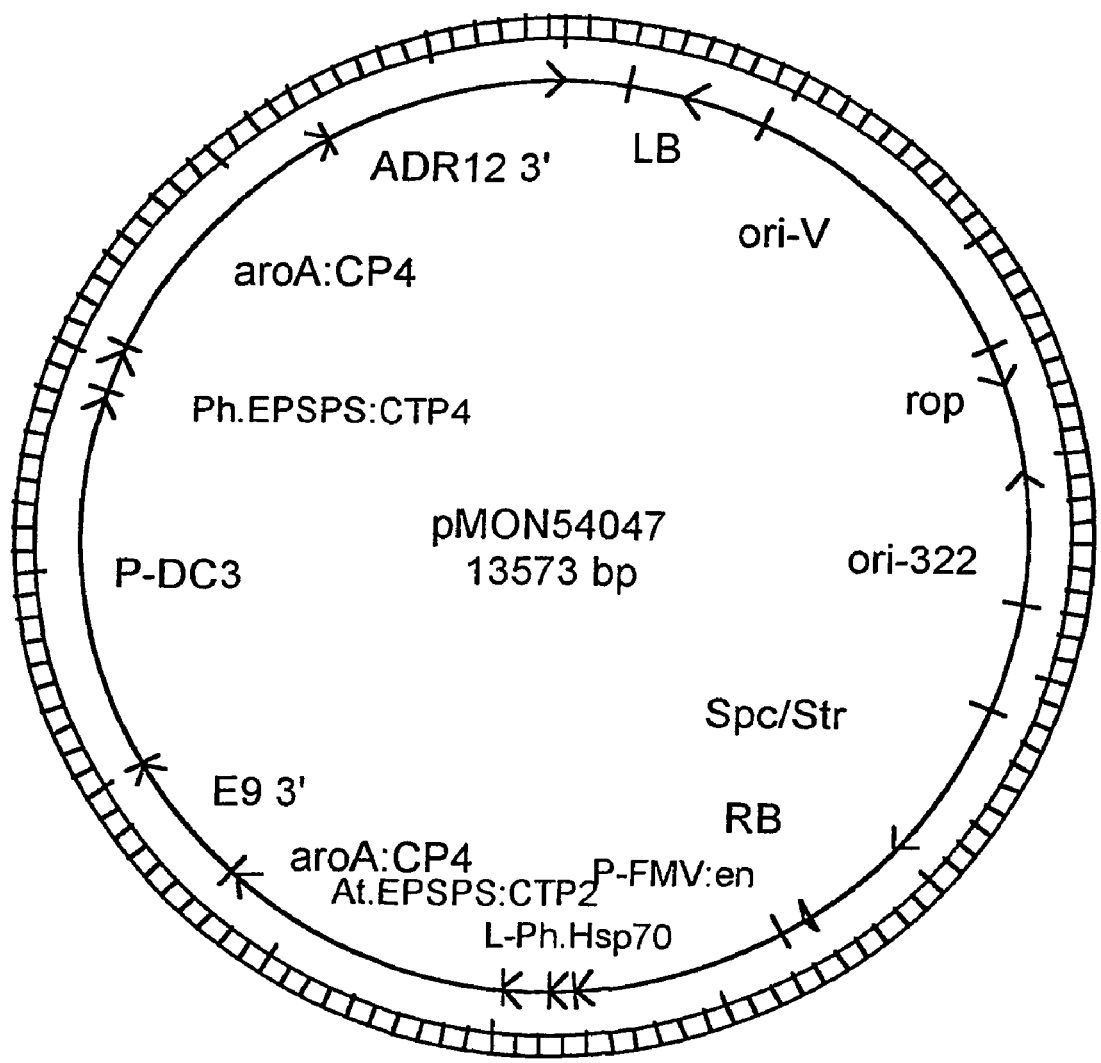
Figure 12:
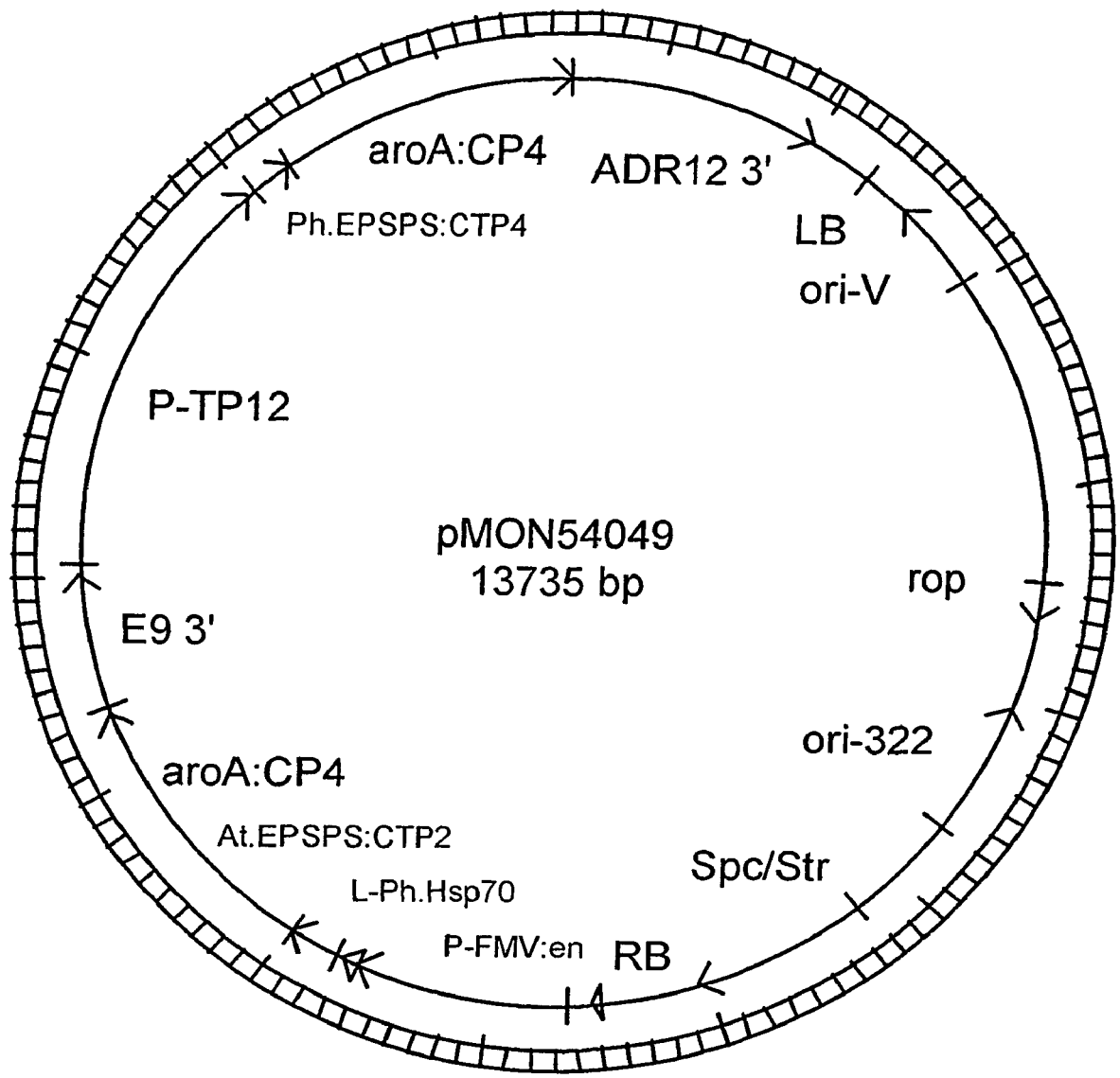

DNA constructs are selected from a plurality of DNA constructs that will perform in a manner predictive of the herbicide tolerance performance observed in *Arabidopsis* for a glyphosate herbicide tolerant phenotype. DNA constructs, for example, pMON15737 (FIG. 1), pMON26140 (FIG. 2), pMON40500 (FIG. 3), pMON40501 (FIG. 4), pMON51915 (FIG. 5), pMON52059 (FIG. 6), pMON52060 (FIG. 7), pMON52065 (FIG. 8), pMON54042 (FIG. 9), pMON54045 (FIG. 10), pMON54047 (FIG. 11), and pMON54049 (FIG. 12) are transformed into *Arabidopsis* plants by vacuum infiltration and into crop plants by *Agrobacterium* mediated methods as described herein for each crop. For measurement of crop plant glyphosate tolerance, callus tolerance, vegetative tolerance and reproductive tolerance are scored or rated as good, poor, or percent reproductive tolerance (generally measured as number of seeds produced relative to the unsprayed check plants, except for cotton where a bell plant map rating system is used to measure glyphosate tolerance.

The efficacy of the DNA constructs pMON52059 plant expression cassette P-FMV-At.EF1a/At.CTP2-aroA:CP4/E9 3' and pMON15737 plant expression cassette P-FMV/At.CTP2-aroA:CP4/E93' is compared in transgenic *Arabidopsis thaliana*. The transgenic *Arabidopsis thaliana* plants are produced by the vacuum infiltration (Bechtold et al., C R Acad Paris Life Sci 316: 1194-1199) seeds are potted in soil in trays in a growth chamber adjusted for 24° C., 16 hour light (120 $\mu$E m$^{-2}$s$^{-1}$) cycle to permit normal growth and development of the plants. The pMON52059 V1 event glyphosate tolerant transgenic *Arabidopsis* plants are selected by spray application of glyphosate herbicide at a rate of 24 ounces/acre, the surviving plants are transplanted into individual pots. Eight p-MON5205-9 V1 plants and eight pMON15737 homozygous plants are sprayed a second time corresponding to the observation of bolting, approximately 16 days after the at a rate of 24 ounces/acre. The second spray will determine the efficacy of the two constructs for conferring reproductive tolerance. The plants are observed for vegetative effects of glyphosate application. All plants had complete vegetative tolerance and no abnormal flowers are observed. However, abortion of siliques occurred indicated that seed had not been set in the aborted siliques. The total number of siliques produced by each plant and the siliques that contained seeds (fertile siliques) are counted and tabulated. The results are shown in Table 1 and indicate that the construct pMON52059 demonstrated a greater than 10 fold improvement in fertile siliques, 89% compared to pMON15737 at 8%. The number of fertile fruiting structures is related to the amount of seed that can be produced, this is especially important in crops whose yield is associated with seed numbers. Crops such as cotton, soybean, canola, wheat, and corn are crops where reproductive tolerance to glyphosate is essential for good yield.

TABLE 1

Comparison of the hybrid promotoer P-FMV EF1a (pMON52059) and P-FMV (pMON15737) in conferring reproductive tolerance to glyphosphate in *Arabidopsis* plants.

| | pMON52059 | | | | pMON15737 | | |
|---|---|---|---|---|---|---|---|
| Plant Number | Fertile Siliques | Total Siliques | Percent Fertility | Plant Number | Fertile Siliques | Total Siliques | Percent Fertility |
| 8819 | 39 | 50 | 78.0% | 1 | 74 | 540 | 13.7% |
| 8820 | 626 | 691 | 90.6% | 2 | 23 | 600 | 3.8% |
| 8821 | 507 | 561 | 90.4% | 3 | 1 | 470 | 0.2% |
| 8822 | 0 | 69 | 0.0% | 4 | 20 | 646 | 3.1% |
| 8823 | 512 | 534 | 95.9% | 5 | 43 | 717 | 6.0% |
| 8827 | 326 | 354 | 92.1% | 6 | 22 | 651 | 3.4% |
| 8833 | 432 | 461 | 93.7% | 7 | 178 | 868 | 20.5% |
| 8838 | 323 | 374 | 86.4% | 8 | 40 | 520 | 7.7% |
| Total | 2765 | 3094 | 89.4% | Total | 401 | 5012 | 8.0% |

Example 5

DNA constructs are transformed into *Arabidopsis* and transgenic lines assayed for vegetative and reproductive tolerance. Selected constructs are transformed into cotton plants, then are tested in a greenhouse spray test using Roundup Ultra™ a glyphosate formulation with a Track Sprayer device (Roundup Ultra is a registered trademark of Monsanto Company). Plants are treated at the "two" true leaf or greater stage of growth and the leaves are dry before applying the Roundup® spray. The formulation used is Roundup Ultra™ as a 3 lb/gallon a.e. (acid equivalent) formulation. The calibration used is as follows:

For a 20 gallons/Acre spray volume:

| | |
|---|---|
| Nozzle speed: | 9501 evenflow |
| Spray pressure: | 40 psi |
| Spray height | 18 inches between top of canopy and nozzle tip |
| Track Speed | 1.1 ft/sec., corresponding to a reading of 1950-1.0 volts. |
| Formulation: | Roundup Ultra ™ (3 lbs. A.e./gallon) |

The spray concentrations will vary, depending on the desired testing ranges. For example, for a desired rate of 8 oz/acre a working solution of 3.1 ml/L is used, and for a desired rate of 64 oz/A a working range of 24.8 ml/L is used. The treated plants are evaluated for vegetative tolerance to glyphosate injury and for reproductive tolerance. Reproductive tolerance is determine by counting the number of first position bolls remaining after treatment for the first five branches.

Of the constructs in Table 2, pMON26140 and pMON52061 show good vegetative tolerance, but no reproductive tolerance in *Arabidopsis*. Constructs demonstrating this phenotype are useful in a hybrid seed production system so pMON26140 was tested in transgenic cotton. The results confirm that vegetative tolerance is good, but reproductive tolerance is markedly reduced. The boll rating of "<1" indicates that less than one cotton boll is set at any first boll position of the first five branches. Of the other constructs in Table 2, pMON40500 and pMON40501 show low vegetative tolerance and no reproductive tolerance in *Arabidopsis* and are not transformed into cotton. pMON51915 and pMON52060 show good vegetative tolerance in *Arabidopsis* and 70% and 78% reproductive tolerance, respectively. These constructs are transformed into cotton and show good vegetative tolerance and 78% first boll retention, nearly identical results as are seen in *Arabidopsis*. This test of the method in cotton confirms this method works to predict construct performance in transgenic cotton for glyphosate tolerance and hybrid seed production systems.

TABLE 2

Comparison of DNA constructs in *Arabidopsis* and Cotton

| DNA Construct | Arabidopsis | | | Cotton | | | |
|---|---|---|---|---|---|---|---|
| | # Lines Tested | Vegetative Tolerance | Reproductive Tolerance | Callus Tolerance | # Lines Tested | Vegetative Tolerance | Reproductive Tolerance |
| pMON26140 | 20 | Good[a] | 0 | Good[b] | 20 | Good | 100% < 1[c] |
| pMON40500 | 11 | Poor | 0 | Poor | | | |
| pMON40501 | 13 | Poor | 0 | Poor | | | |
| pMON51915 | 10 | Good | 70% | Good | 104 | Good | 78% > 1 |
| pMON52060 | 32 | Good | 78% | Good | 36 | Good | 78% > 1 |
| pMON52061 | 10 | Good | 0 | | | | |

[a] fully tolerant, no injury
[b] fully tolerant, generate >50 shoots
[c] boll retention rate Example 6

DNA constructs are transformed into *Arabidopsis* and transgenic lines assayed for vegetative and reproductive tolerance. The same constructs are transformed into tomato to confirm the glyphosate tolerant phenotype observed in *Arabidopsis* relative to tomato (Table 3). Transgenic lines produced from *Arabidopsis* and tomato are treated with a track sprayer at 48 oz/ac or an effective dose of glyphosate at the 5-6 leaf stage or prior to flowering. pMON26140 shows good vegetative tolerance in *Arabidopsis*, low vegetative tolerance in tomato, and no reproductive tolerance in either plant. pMON52065, pMON51915, and pMON52060 show good vegetative and reproductive tolerance in *Arabidopsis* and similarly good tolerance in tomato (percent seed set relative to unsprayed check). In tomato, where seed production does not affect fruit yield, unless it is 0 or less than one seed/flower, the values of >30% are acceptable because the fruit yield is equivalent to the unsprayed check plants. The lower numbers of seeds in some tomato varieties may be a desirable trait.

TABLE 3

Comparison of DNA constructs in *Arabidopsis* and tomato.

| DNA Construct | Arabidopsis | | | Tomato | | | |
|---|---|---|---|---|---|---|---|
| | # Lines Tested | Vegetative Tolerance | Reproductive Tolerance | Callus Tolerance | # Lines Tested | Vegetative Tolerance | Reproductive Tolerance |
| pMON26140 | 20 | Good | 0 | Good | 85 | 20% | 0 |
| pMON52065 | 29 | Good | 82% | Good | 802 | | 35% |
| pMON51915 | 10 | Good | 70% | Good | 134 | | 32.8% |
| pMON52060 | 32 | Good | 78% | Good | 391 | 73% | 38.9% |

Example 7

The DNA constructs, pMON26140, pMON40500, pMON40501, pMON51915, pMON52050, and pMON52060 are transformed into *Arabidopsis* and soybean to confirm the method of the present invention for use in soybean (Table 4). DNA constructs, pMON40500 and pMON40501 show poor vegetative tolerance in *Arabidopsis* and no reproductive tolerance. The same two constructs also show poor soybean embryo tolerance to glyphosate, and in whole soybean plants the vegetative tolerance was poor and the plants did not reach reproductive maturity. pMON26140 shows good vegetative tolerance in *Arabidopsis*, but no reproductive tolerance. This construct shows a similar activity in soybean. The constructs, pMON51915, pMON52059 and pMON52060 show good vegetative and reproductive tolerance in *Arabidopsis* and the first two of these constructs have similar efficacy in soybean. Soybean plants transformed with pMON51915 also showed good vegetative tolerance to glyphosate, but were not tested for reproductive tolerance.

TABLE 4

Comparison of DNA constructs in *Arabidopsis* and soybean.

| | *Arabidopsis* | | | Soybean | | |
|---|---|---|---|---|---|---|
| DNA Construct | # Event Tested | Vegetative Tolerance | Reproductive Tolerance | Embryo Tolerance | Vegetative Tolerance | Reproductive Tolerance |
| pMON26140 | 20 | Good | 0 | Good | Good | 0 |
| pMON40500 | 11 | Poor | 0 | Poor | Poor | — |
| pMON40501 | 13 | Poor | 0 | Poor | Poor | — |
| pMON51915 | 10 | Good | 70% | Good | Good | Good |
| pMON52059 | 8 | Good | 87.5% | Good | Good | Good |
| pMON52060 | 32 | Good | 78.1% | Good | Good | — |

Example 8

The DNA constructs (Table 5), pMON26140 and pMON51915 transformed into *Arabidopsis* and tobacco, then treated with an effective dose of glyphosate show good correlation between vegetative tolerance and reproductive tolerance to glyphosate, demonstrating that the method of the present invention is effective for selecting constructs for glyphosate tolerance in tobacco.

TABLE 5

Comparison of DNA constructs in *Arabidopsis* and tobacco.

| | *Arabidopsis* | | | Tobacco | | | |
|---|---|---|---|---|---|---|---|
| DNA Construct | # Event Tested | Vegetative Tolerance | Reproductive Tolerance | # Event Tested | Callus Tolerance | Vegetative Tolerance | Reproductive Tolerance |
| pMON26140 | 20 | Good | 0 | 16 | Good | Good | 0 |
| pMON51915 | 10 | Good | 70% | 17 | Good | Good | 82.4% |

The above results demonstrate that a method for selecting DNA constructs conferring herbicide tolerance in *Arabidopsis* is predictive for the DNA constructs performance in crop plants. Preferably, the method of the present invention is related to glyphosate tolerance in dicot crops.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

The invention claimed is:

1. A method of selecting a DNA construct effective for conferring herbicide tolerance in a crop plant from a plurality of DNA constructs, said method comprising:
   i) transforming a plant cell of a model plant with a DNA construct comprising a first DNA molecule that functions as a promoter of RNA transcription in a plant cell, operably linked to a second DNA molecule encoding a herbicide tolerance protein, operably linked to a third DNA molecule providing transcription termination in a plant cell;
   ii) growing the transformed plant cell of model plant into a transformed whole model plant;
   iii) treating the transformed whole model plant prior to flower formation with an effective dose of a herbicide for which the herbicide tolerance gene is effective;
   iv) scoring the transformed whole model plant for vegetative damage and reproductive fertility;
   v) performing steps i-iv with at least one other DNA construct containing the same second DNA molecule encoding a herbicide tolerance protein but different in at least one of the first or third DNA molecules; and
   vi) selecting at least one of said DNA constructs that provides a high level of herbicide tolerance to vegetative damage and a high level of herbicide tolerance to reproductive damage to the transformed whole model plant.

2. The method of claim 1 wherein said model plant is selected from the group consisting of *Arabidopsis* and microtomato.

3. The method of claim 1, wherein said herbicide tolerance protein confers plant cell tolerance to glyphosate, glufosinate, sulfonylureas, imidazolinones, bromoxynil, dalapon, cyclohexanedione, protoporphyrinogen oxidase inhibitors, or isoxaflutole.

4. The method of claim 3, wherein said second DNA molecule is a glyphosate resistant EPSP synthase.

* * * * *